United States Patent [19]

Hu

[11] 4,319,569
[45] Mar. 16, 1982

[54] FASTER IRRIGATION SET FOR CONTROLLING COLOSTOMY

[76] Inventor: Hsueh-Shun Hu, 4th Fl., No. 16, Lane 220, Section 2, Hsin-Lung Rd., Taipei, Taiwan

[21] Appl. No.: 116,153

[22] Filed: Jan. 28, 1980

[51] Int. Cl.³ .............................................. A61M 3/00
[52] U.S. Cl. ..................................... 128/241; 128/283
[58] Field of Search ............... 128/240, 241, 283, 227, 128/294, 295

[56] References Cited

U.S. PATENT DOCUMENTS

| | | | |
|---|---|---|---|
| 1,184,970 | 5/1916 | Larssen | 128/240 |
| 2,874,696 | 2/1959 | Bried | 128/227 |
| 3,771,522 | 11/1973 | Waysilk et al. | 128/240 |
| 3,780,736 | 12/1973 | Chen | 128/227 |
| 3,916,897 | 11/1975 | Elmore et al. | 128/283 |
| 4,050,461 | 9/1977 | Ruby | 128/227 |
| 4,134,404 | 1/1979 | Williams, Jr. | 128/283 |
| 4,157,717 | 6/1979 | Goldberg | 128/227 |

*Primary Examiner*—Robert W. Michell
*Assistant Examiner*—J. L. Kruter
*Attorney, Agent, or Firm*—Browdy and Neimark

[57] ABSTRACT

A faster irrigation set for controlling Colostomy, has a water speed controlling device and an excrement suction device provided between the irrigating bag and the catheter which has a plurality of holes formed on the surface thereof for passing excrement. The excrement suction device has a valve regulating the performance of the inserted catheter either for excrement suction or irrigation.

12 Claims, 2 Drawing Figures

FASTER IRRIGATION SET FOR CONTROLLING COLOSTOMY

BACKGROUND OF THE INVENTION

The present invention relates to the improvements in a stoma irrigation set for controlling Colostomy.

The conventional stoma irrigation sets for controlling Colostomy cannot be operated both for irrigating and drawing-off excrement with the catheter. It takes much time for a patient to perform the irrigating and withdrawal of excrement procedures using those well-known irrigation sets. Generally the whole procedure including irrigation with physiological salt solution and complete withdrawal of excrement takes about 1-2 hours or even more. Furthermore, the speed of the flowing irrigation solution cannot be easily controlled and sometimes the flowing may interrupt, and even worse a counterflowing of the irrigating solution may occur due to the inner pressure of the large intestine. Besides, irrigation using such known set has the problem of unexpected excrement taking place during the period of irrigation and the disadvantage of not being capable of completing the excretion of withdrawal in single performance.

SUMMARY OF THE INVENTION

The primary object of the present invention, therefore is to provide a device which can facilitate the procedure of irrigation and shorten the withdrawal time of excrement.

Another object of this invention is to provide a device for controlling the speed of flowing irrigating solution and avoid intermitting and counter-flowing of irrigating solution caused by the inner pressure of the large intestine.

Still another object of this invention is to provide a device for hindering the accompanied excrement during irrigation.

Yet further object of this invention is to provide a device for emptying the excrement in a single performance.

These and other important objects of this invention will become apparent from the following specification, when taken in connection with the appended drawings illustrating a preferred embodiment of the device of this invention.

The present Colostomy device comprises an irrigating solution container, means for controlling the speed of the flowing irrigating solution, means for excrement suction, a catheter having a plurality of holes thereon, means for fixing the catheter and tightening around the stoma and means for regulating the flowing direction either for irrigating solution or drawing the excrement off.

DETAILED DESCRIPTION OF THE INVENTION

Figure 1:
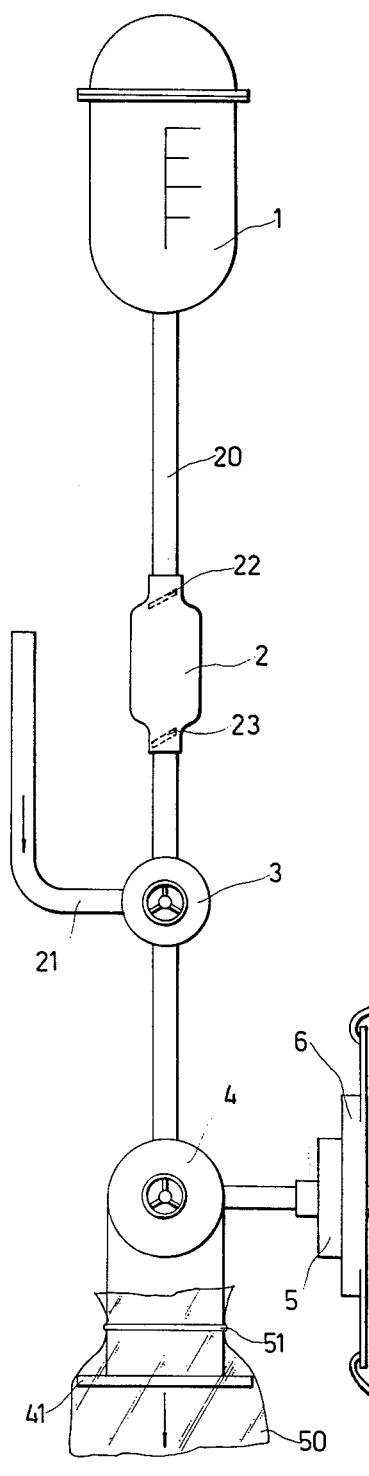
FIG. 1 is a schematic illustration of the device of this invention.
Figure 2:
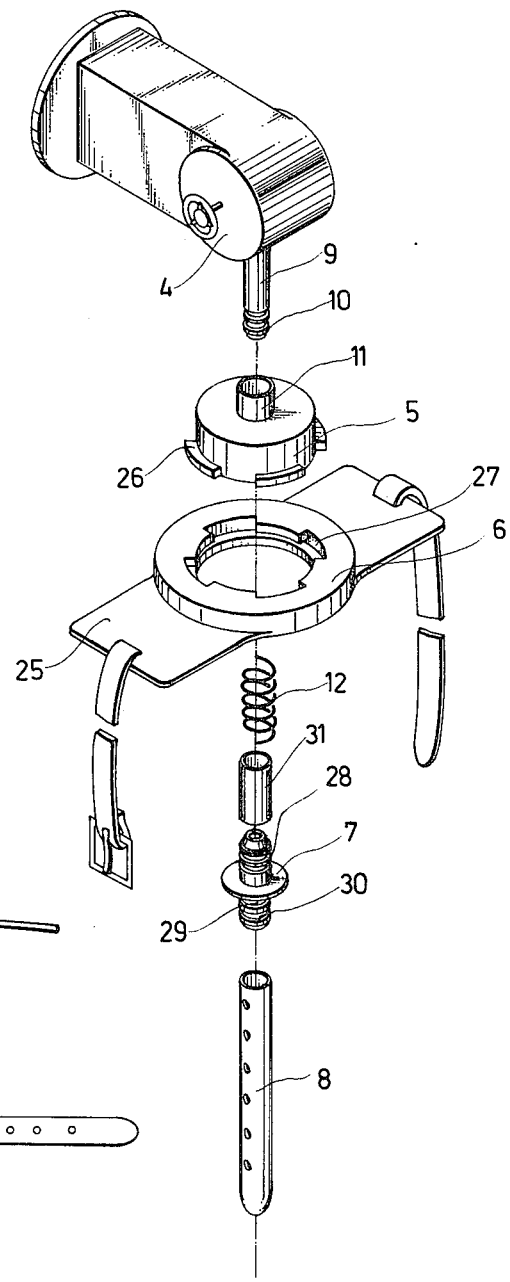
FIG. 2 is an exploded view of the parts of means for fixing the catheter and tightening around the stoma.

Reference is now made to FIGS. 1 and 2, which describe an embodiment of the device of this invention.

As shown in FIG. 1, the irrigating container (1) is connected to a rubber squeezer bulb (2) by a connecting tube (20). Between the rubber squeezer bulb (2) and a second 3-direction valve (4) is first 3-direction valve (3). The first 3-direction valve (3) has also a tube (21) connected thereto for leading to the faucet (not shown in the drawings). The rubber squeezer bulb (2) has a pair of check valves (22) (23) provided respectively at its two ends.

The tube (9) connected to other end of the second 3-direction valve (4) has a zigzag-shaped surface provided on its end (10) as shown in FIG. 2. The cap (5) has a protruded tube (11) on the center thereof. The flange of the cap (5) has tooth-shaped protrusions (26) which are fitted to the tooth-shaped recesses (27) on the inner ring edge portion of the face plate (6) of the face plate belt (25). The cap (5) can fix with the face plate very tightly by fitting protrusions (26) mating with the recesses (27).

The stoma plate (7) has respectively a protruded tube at each side, one side protruded tube (28) being sleeved with a spring (12) and both protruded tubes (28) and (29) having zigzag-shaped surface provided thereon. A rubber tube (31) is connected between the tube (28) and the end (10) of the valve (4). The open end (30) of the tube (29) is connected with the catheter (8). The catheter (8) has a plurality of holes thereon. The means for fixing the catheter and tightening around the stoma comprises the cap (5), the face plate belt (6) and the stoma plate (7). When the means for fixing the catheter and tightening around the stoma is assemblied and secured on the body, the spring (12) is thrust through the hole of the face plate (6) to the inner side of the top portion of the cap (5), and the protruded tube (29) is connected by using a tube (not shown in FIG.) which being able to slide through the tube (11) to the end (10) of the tube (9).

When irrigating is performed, the first valve (3) and the second valve (4) are turned so that the physiological salt solution can controllably flow into the large intestine through a plurality of holes on the catheter. It is to be noted that no counter-flowing can occur due to the function of the check valves provided at the both ends of the rubber squeezer. After the irrigating step is completed, both valves (3) and (4) are turned 90 degrees so that the water from the faucet flows through (the direction is shown as the arrow in FIG. 1) and spurt into the toilet. Such water flow, as it moves across the end face of the tube 9, induces lower pressure in the tube (9) and the excrement is drawn off into the toilet.

Therefore, the catheter in the present invention can be used as both irrigation and excretion of withdrawal. On the end (41) of the valve (4), there may be attached a plastic bag (50) which is tightened onto said end (41) by a rubber band (51). This bag (50) is used for preventing soiling of the clothes by the excrement.

It is to be understood that this invention is capable of extended application and is not confined to the exact showing of the drawings nor to the precise construction described and therefore, such changes and modifications may be made therein as do not affect the spirit of the invention nor exceed the scope thereof as expressed in the appended claims.

What I claim is:

1. An irrigation set for a colostomy patient comprising an irrigating solution container and a catheter, means for controlling the speed of irrigating solution from said container to said catheter, means for effecting suction of excrement through said catheter, means for fixing said catheter and tightening around the stoma, and means for regulating the flowing direction either for irrigating solution or drawing the excrement off, wherein said means for fixing the catheter and tightening around the stoma comprises a cap having a flange, a face plate belt having an apertured face plate with an inner ring for mating with said cap, and a stoma plate having a tube protruding from one side thereof; the flange of the said cap and the inner ring edge of the said face plate having corresponding protrusions and recesses for said mating; said stoma plate being connected to said cap and face plate with said protruding tube of the said stoma plate therebetween, said protruding tube being sleeved with a spring to urge said stoma plate away from said face plate.

2. An irrigation set according to claim 1, wherein, the catheter has a plurality of holes thereon.

3. An irrigation set according to claim 1 wherein, the means for controlling the speed of irrigating solution is a squeezer, both ends of said squeezer being provided with a check valve.

4. An irrigation set according to claim 1, wherein, said spring being thrusted through the hole of the faceplate to the inner side of the top portion of said cap, while secured around the stoma.

5. An irrigation set according to claim 1, wherein, means for regulating the flowing direction either for irrigating solution or drawing the excrement off are valves.

6. An irrigation set according to claim 5, wherein said cap has a protruded tube, and one valve has a side tube connected to said protruded tube of said stoma plate by a tube sliding through said protruded tube of said cap.

7. An irrigation set according to claim 1, wherein, said protruding tube of the said stoma plate has a zigzag-shaped surface.

8. An irrigation set for a colostomy patient comprising:
an irrigating solution container;
means for controlling the speed of irrigating solution which has a first and a second open end thereof, the first open end thereof communicating with the irrigating solution container;
means for suctioning excrement and regulating the flow direction comprising first and second three-way valves which are connected in series with the second open end of the controlling means;
a catheter; and
means for fixing the catheter and tightening it around the stoma comprising a cap which has a protruded tube on the center thereof and a flange portion, the flange portion being provided with a plurality of protrusions; a face plate belt having a ring-shaped face plate, on the inner ring edge portion thereof being a plurality of corresponding recesses provided for fitting the protrusions of the cap; a stoma plate having a protruded tube on each side thereof respectively, the protruded tube of one side being sleeved with a spring member, one said protruded tube of said stoma plate passing through the protruded tube of the cap with the cap fixed with the face plate belt, the spring being thrust against the inner side of the top portion of the cap, the protruded tube of the other side being connected to the catheter, whereby in case of irrigation the irrigating solution flows controllably through the catheter into the stoma, and in case of excrement suction the three-way valves are regulated to let the water flow therethrough without passing into said catheter and thereby inducing a lower pressure in said catheter to suction the excrement together with the flowing water to the toilet.

9. An irrigation set according to claim 8, wherein the spring-sleeved protruded tube of the stoma plate is connected with a tube which can pass through the protruded tube of the cap to connect one way of the three-way valve.

10. An irrigation set according to claim 8, wherein the protruded tube of the stoma plate has a zigzag outer surface.

11. An irrigation set according to claim 8, wherein the catheter has a plurality of holes provided thereon.

12. An irrigation set according to claim 8, wherein the speed controlling means is a squeezer provided with a check valve at each end thereof.

* * * * *